(12) United States Patent
Horiuchi

(10) Patent No.: US 7,273,373 B2
(45) Date of Patent: Sep. 25, 2007

(54) ARTIFICIAL ROOT OF A TOOTH

(75) Inventor: Kikuji Horiuchi, Numazu (JP)

(73) Assignee: K. K. Hollyx, Numazu-shi, Shizuoka (JP)

(*) Notice: Subject to any disclaimer, the term of this patent is extended or adjusted under 35 U.S.C. 154(b) by 252 days.

(21) Appl. No.: 10/693,492

(22) Filed: Oct. 27, 2003

(65) Prior Publication Data

US 2004/0091837 A1   May 13, 2004

(30) Foreign Application Priority Data

Oct. 31, 2002   (JP) .............................. 2002-316912

(51) Int. Cl.
*A61C 8/00*   (2006.01)

(52) U.S. Cl. ........................................ 433/174; 433/173

(58) Field of Classification Search ................ 433/174, 433/175
See application file for complete search history.

(56) References Cited

U.S. PATENT DOCUMENTS

| 4,229,169 | A  | * | 10/1980 | Smith et al. ................. 433/174 |
| 4,334,865 | A  | * | 6/1982  | Borle ........................... 433/221 |
| 6,896,517 | B1 | * | 5/2005  | Bjorn et al. ................. 433/174 |
| 6,926,484 | B2 | * | 8/2005  | Kram et al. ................ 411/311 |

* cited by examiner

*Primary Examiner*—Cris Rodriguez
*Assistant Examiner*—Candice C. Stokes
(74) *Attorney, Agent, or Firm*—McGinn IP Law Group, PLLC

(57) ABSTRACT

An artificial tooth-root body, having a male thread part to become engaged with a jaw bone and a supporting stage for mounting an artificial tooth, is provided with a self tapping part, in order to maintain the stable mounting status for a long time by preventing the loosening due to secular distortion, and to reduce the laborious and long-time therapy.

7 Claims, 6 Drawing Sheets

ARTIFICIAL ROOT OF A TOOTH

BACKGROUND OF THE INVENTION

1. Field of the Invention

The present invention relates to an artificial root of a tooth (dental implant) used for so-called "implant therapy" in the field of dental surgery. More particularly, the present invention relates to an artificial root of a tooth which may maintain the stable mounting status for a long time, after implant therapy.

2. Description of the Related Art

An example of implant therapy in the dentistry field will be first explained with reference to FIG. 6. There is a jaw bone 101, into which a hole 103 at a predetermined diameter has been drilled, and a female thread part has been formed on the surface of the hole 103. An artificial root of a tooth 105 is inserted in the hole 103, and is engaged with the hole 103 to be secured thereto. The artificial root of the tooth 105 has a male thread part 107 to be engaged with the female thread part of the hole 103, and also has a support stage 109 formed at the top of thereof. The support stage 109 has a hole drilled inside, on which surface a female thread part has been formed.

There is an artificial tooth 111, and a tooth mounting 113, provided with a male thread part formed thereon, has been attached to the lower part of the artificial tooth 111. Thus, the artificial root of the tooth 105 has been engaged with and secured to the jaw bone 101 in advance, and the female thread part of the support stage 109 of the artificial root of the tooth 105 becomes engaged with the male thread part of the tooth mounting 113 of the artificial tooth 111, whereby the artificial tooth 111 may be secured to the artificial root of the tooth 105.

However, the above prior art has the following disadvantages.

First, the artificial root of the tooth 105, which was once engaged with and secured to the jaw bone 101, would become loosened due to secular distortion, whereby the secured artificial tooth 111 would become unstable mounting.

Second, in order to engage the artificial root of the tooth 105 with the hole 103 of the jaw bone 101, the female thread part must be formed on the surface of the hole 103, which required a complicated, laborious and long-time surgery treatment.

SUMMARY OF THE INVENTION

It is an object of the present invention to provide an artificial root of a tooth, which may maintain the stable mounting status for a long time by preventing the loosening due to secular distortion, and which may reduce the complicated and laborious surgery treatment, so that the time required for therapy may be reduced.

To achieve the object mentioned above, according to claim 1 of the present invention, there is provided an artificial root of a tooth, comprising an artificial root body of a tooth provided with a male thread part to be engaged with a jaw bone and with a supporting stage on which an artificial tooth is mounted, and a self tapping part provided on the artificial root body of the tooth.

According to claim 2, there is provided the artificial root of the tooth as claimed in claim 1, wherein the self tapping part is a first self tapping part provided at the top of the artificial root body of the tooth.

According to claim 3, there is provided the artificial root of the tooth as claimed in claim 1, wherein the self tapping part is a second self tapping part in a saw-blade shape, provided on a screw thread of the male thread part.

According to claim 4, there is provided the artificial root of the tooth as claimed in claim 1, wherein the self tapping part comprising, a first self tapping part provided at the top of the artificial root body of the tooth, and a second self tapping part in a saw-blade shape provided on a screw thread of the male thread part.

According to claim 5, there is provided the artificial root of the tooth as claimed in claim 1 or claim 4, wherein the first self tapping part comprising a triple blade.

According to claim 6, there is provided the artificial root of the tooth as claimed in claim 3 or claim 4, wherein the screw thread of the male thread part has a section on the side of the base end of the screw thread, at which the second self tapping part in a saw-blade shape is not provided.

According to claim 7, there is provided the artificial root of the tooth as claimed in claim 6, wherein the screw thread of the male thread part has a section on the side of the base end of the screw thread, positioned at the first crest or from the first crest to the halfway of the second crest counted from the base end of the screw thread, at which the second self tapping part in a saw-blade shape is not provided.

Therefore, according to the present invention, the artificial root of the tooth is provided with the artificial root of a tooth, comprising the artificial root body of the tooth having the male thread part to be engaged with the jaw bone and also having the supporting stage on which the artificial tooth is mounted, and with the self tapping part on the artificial root body of the tooth. Therefore, the self tapping part may cut the thread by itself and become engaged with the jaw bone, and after engagement, the cut particles of the jaw bone may go inside the recess part of the self tapping part. The bone particles may grow and eventually form the new bone at the recess part, whereby the stable mounting status may be obtained.

The self tapping part may comprise, the first self tapping part provided at the top of the artificial root body of the tooth, or the second self tapping part in a saw-blade shape, provided on the screw thread of the male thread part, or both the first and the second self tapping parts.

In any case, because the thread cutting mechanism has been added to the artificial root of the tooth, it is no longer necessary to form the female thread part in advance. Further, the cut particles of the jaw bone would go inside the recess part of the first self tapping part, or inside the recess part in the saw-blade shape of the second self tapping part, where the bone particles may grow and eventually form the new bone, thereby the stable mounting status may be obtained.

For example, the first self tapping part may preferably comprise a triple blade.

Further, when the screw thread of the male thread part has a section at the base end of the screw thread, at which the second self tapping part in a saw-blade shape is not provided, it is possible to prevent the deposition of bacteria or food waste particles at that part.

BRIEF DESCRIPTION OF THE DRAWINGS

The invention will be described below in detail with reference to the accompanying drawings, in which:

FIG. 3 is views according to the first embodiment of the present invention, wherein

DETAILED DESCRIPTION OF THE INVENTION

FIRST EMBODIMENT

Figure 1:
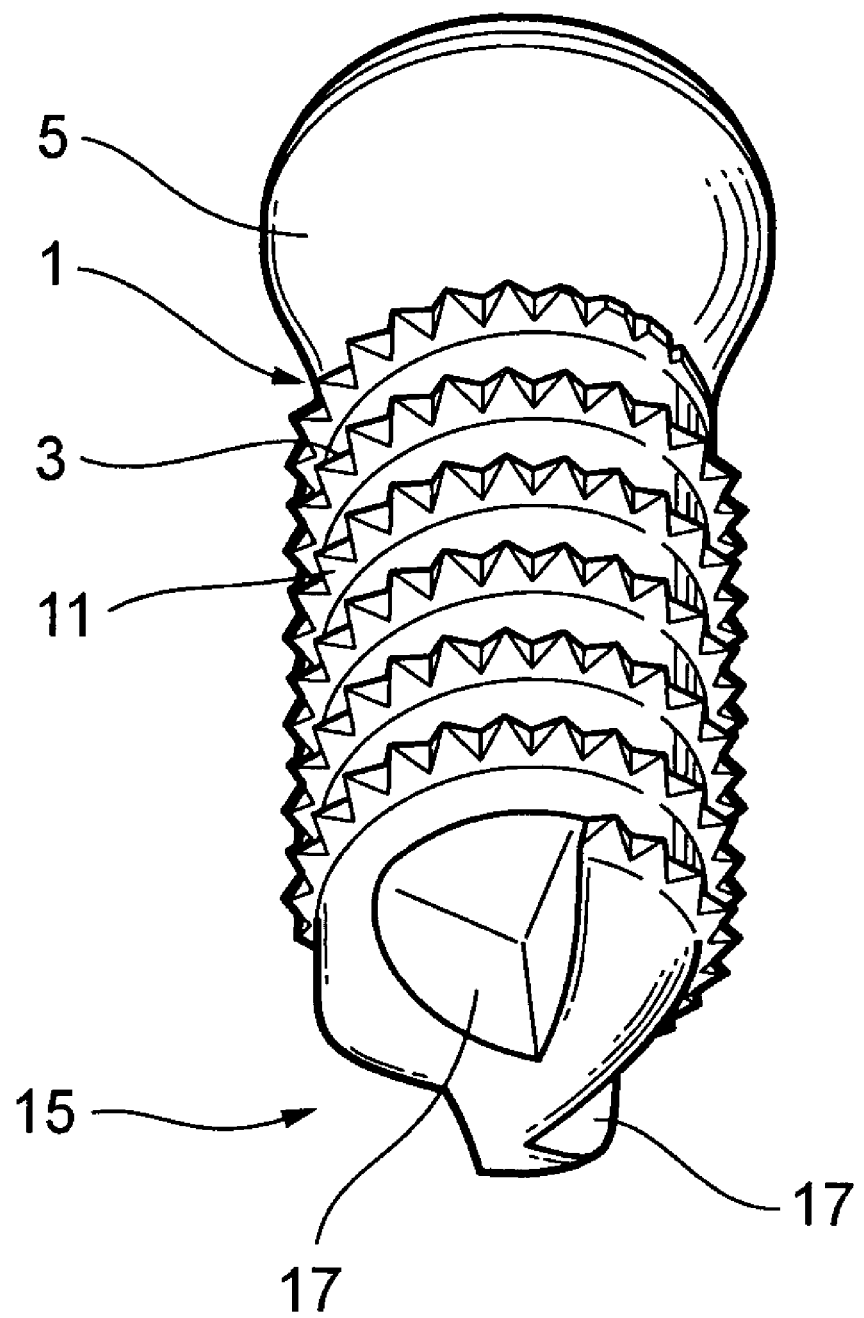
FIG. 1 is a perspective view, showing an overall structure of an artificial root of a tooth according to a first embodiment of the present invention.
Figure 2:
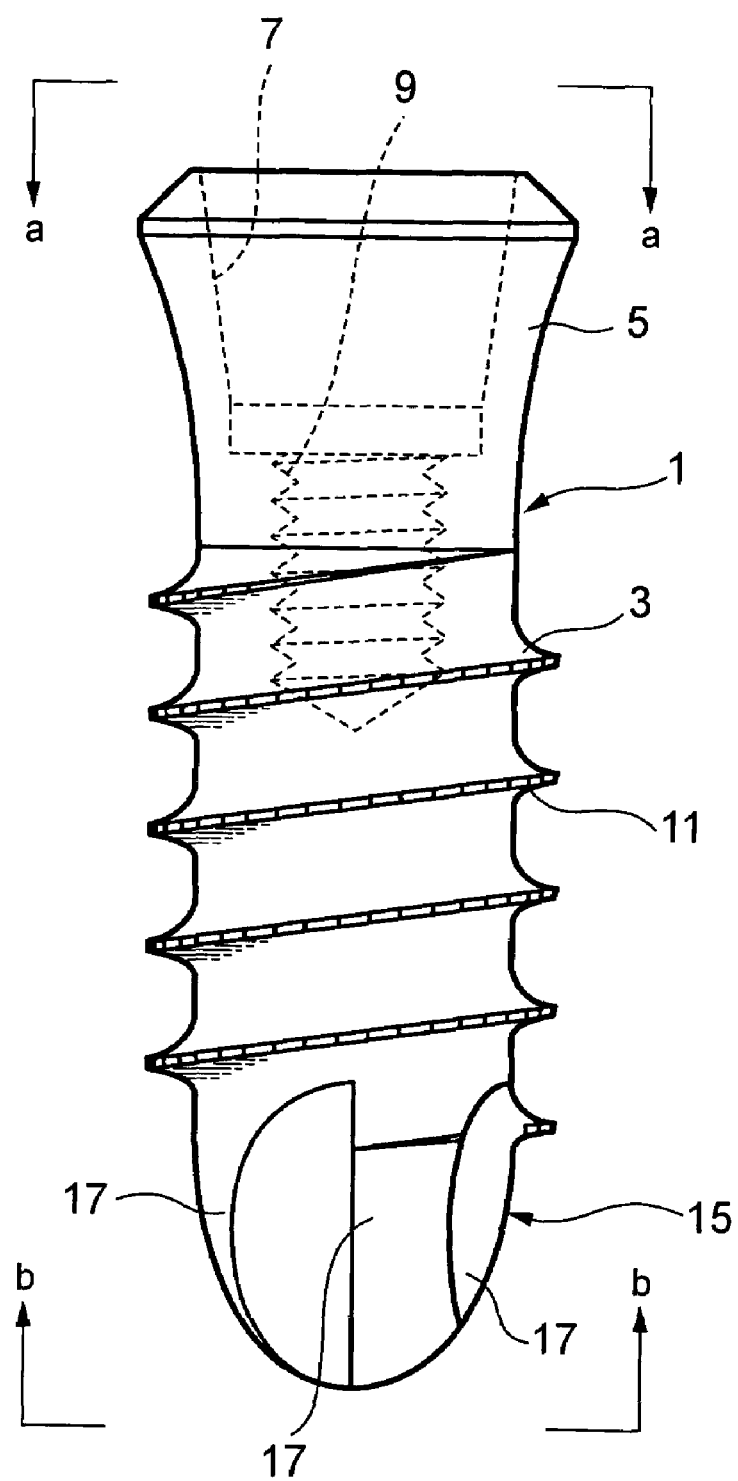
FIG. 2 is a front view, showing an overall structure of the artificial root of the tooth according to the first embodiment of the present invention.
Figure 3A:
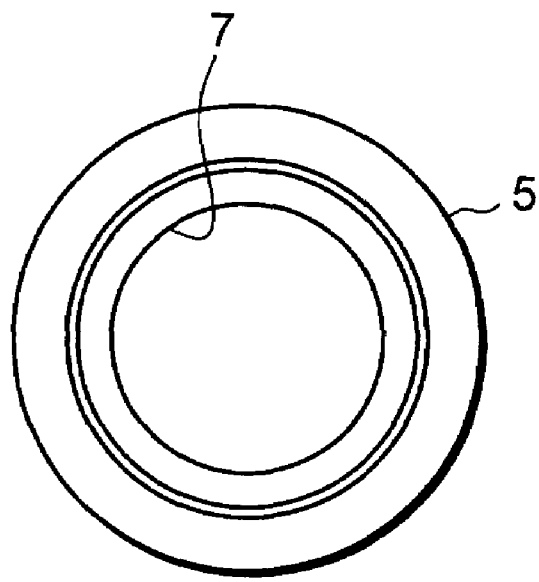
FIG. 3(a) is a view as viewed by an arrow a-a of FIG. 2.

A first embodiment of the present invention will now be described with reference to FIGS. 1 through 3. FIG. 1 is a perspective view showing a structure of an artificial root of a tooth according to the first embodiment, and FIG. 2 is a front view of the artificial root of the tooth. There is an artificial root body of a tooth 1 in an axial shape, having a male thread part 3 in order to become engaged with a hole (not shown) which has been formed in the jaw bone in advance. The artificial root body of the tooth 1 also has a supporting stage 5 at the base, on which an artificial tooth (not shown) may be mounted. The supporting stage 5 has a hole 7 drilled inside, on which surface a female thread part 9 has been formed. Thus, a tooth mounting of the artificial tooth (not shown) is inserted in the hole 7, and the artificial tooth is engaged with and secured to the female thread part 9, via the male thread part formed on that artificial tooth.

Figure 3B:
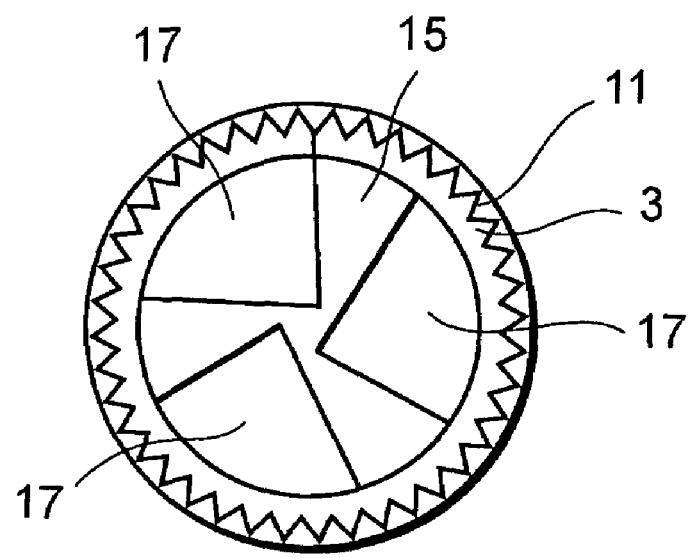
FIG. 3(b) is a view as viewed by an arrow b-b of FIG. 2.

As illustrated in FIGS. 1, 2 and 3(b), each of crests of the male thread part 3 is in a saw-blade shape, serving as a second self tapping part 11. Further, there is a first self tapping part 15 provided at the top of the artificial root body of the tooth 1. The first self tapping part 15 has a triple blade structure, and as illustrated in FIG. 3(b), there are three blades 17 provided at even intervals to each other. Thus, when the first self tapping part 15 and the second self tapping part 11 are screwed into a hole, which has been formed in advance in the jaw bone (not shown), the first self tapping part 15 and the second self tapping part 11 will form a female thread part on the surface of that hole, whereby the first self tapping part 15 and the second self tapping part 11 become engaged with the formed female thread part.

The function of the present embodiment will be explained with reference to the structure as discussed above.

First, when the implant therapy is done, a hole at a predetermined diameter is first drilled at a predetermined position of the jaw bone (not shown). Thereafter, the artificial root of the tooth according to the present embodiment is inserted into the drilled hole. At that time, the first self tapping part 15 and the second self tapping part 11 will form the female thread part on the surface of the hole, whereby the first self tapping part 15 and the second self tapping part become engaged with the formed female thread part. When the artificial root of the tooth is engaged with and secured to the hole of the jaw bone, the artificial tooth (not shown) is mounted on the supporting stage 5. Thereafter, the necessary treatment will be given, and the implant therapy will be completed.

When the artificial root of the tooth is mounted according to the above method, with reference to the first self tapping part 15 and the second self tapping part 11, the bone particles, which have been formed during the forming of the female thread part, will go inside the recess part of the first self tapping part 15 and that of the second tapping part 11. In addition, the jaw bone will newly grow and also go into the first self tapping part 15 and the second self tapping part 11, whereby the new bone will be formed. Consequently, the stable mounting status of the artificial root of the tooth may be obtained.

In particular, the bone particles will go into three spaces between the three blades 17 of the first self tapping part 15, and the jaw bone will newly grow and also go into these spaces, whereby the new bone will be formed there. Similarly, the bone particles will also go into the recess part of the saw-blade shape of the second self tapping part 11, into which the jaw bone will newly grow and form the new bone.

The present embodiment has the following merits.

First, the bone particles will go, into the spaces between the three blades 17 of the first self tapping part 15, as well as into the saw-blade shape part of the second self tapping part 11. In addition, the jaw bone will newly grow and go into the spaces and saw-blade shape part, whereby the stable mounting status may be obtained. Therefore, it is possible to provide the stable secured status for a long time, not only for the artificial root of the tooth, but also for the artificial tooth in itself.

Second, because the first self tapping part 15 and the second self tapping part 11 may form the female thread part on the jaw bone by themselves, it is not necessary to form such a female thread part in advance. Consequently, the therapy will be facilitated, and the therapy time will be reduced.

Third, as compared with the case of being engaged with the female thread part which has been formed in advance, when the artificial root of the tooth forms the female thread part by itself and becomes engaged with the female thread part formed thereby, it is possible to obtain stronger securing status. This is because the male thread part 3 of the artificial root of the tooth becomes in stronger and tighter contact with the formed female thread part.

SECOND EMBODIMENT

Figure 4:
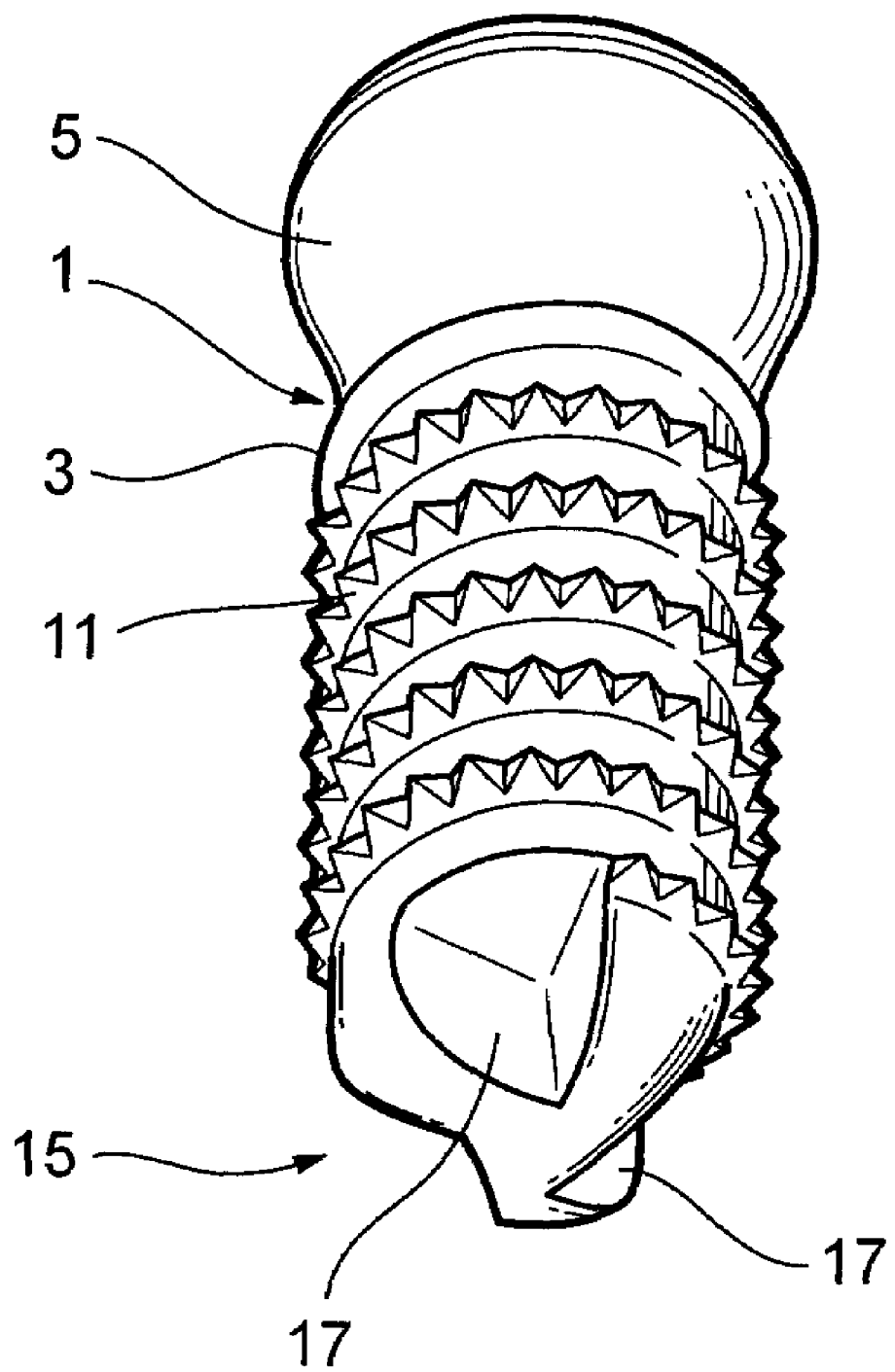
FIG. 4 is a perspective view, showing an overall structure of an artificial root of a tooth according to a second embodiment of the present invention.
Figure 5:
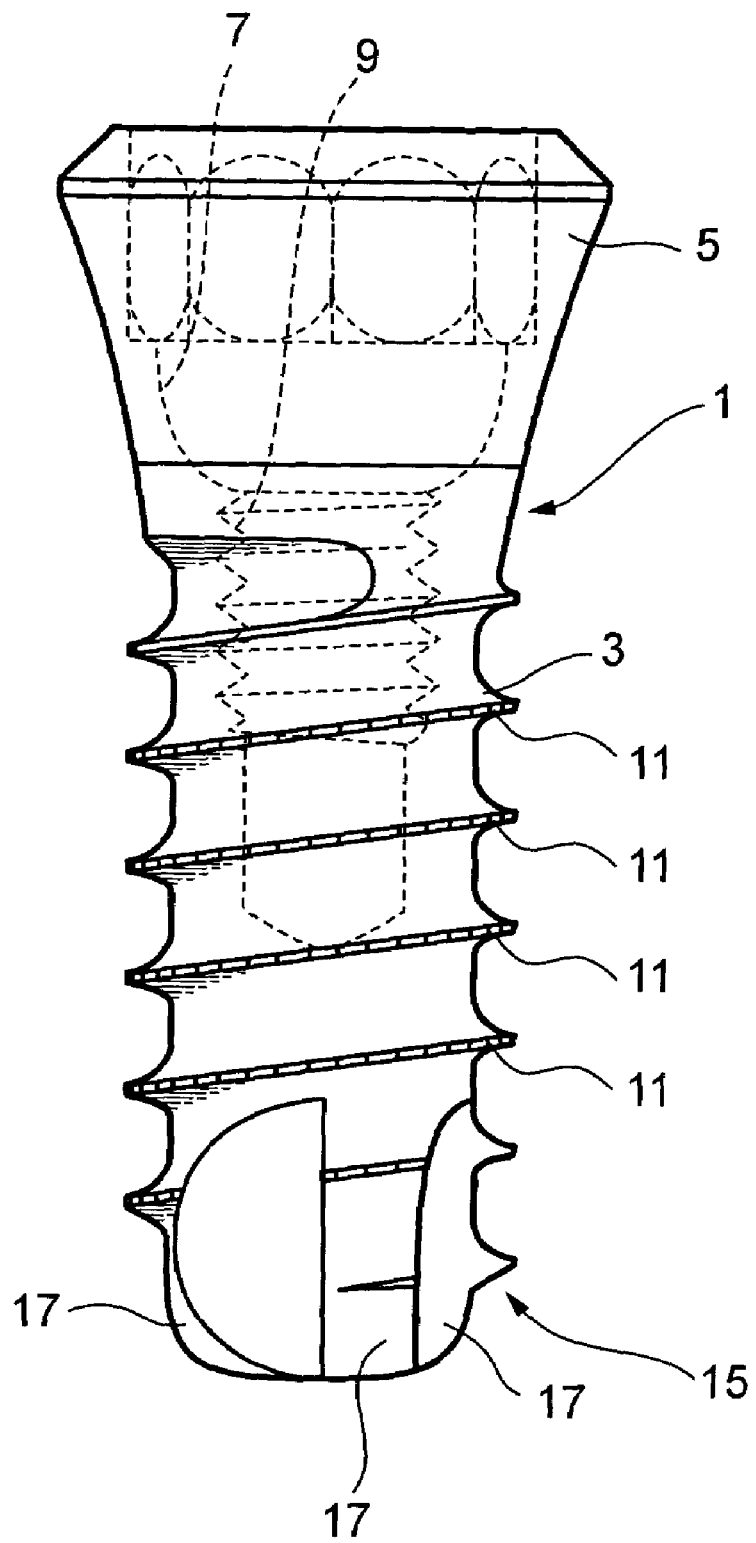
FIG. 5 is a front view, showing an overall structure of the artificial root of the tooth according to the second embodiment of the present invention.
Figure 6:
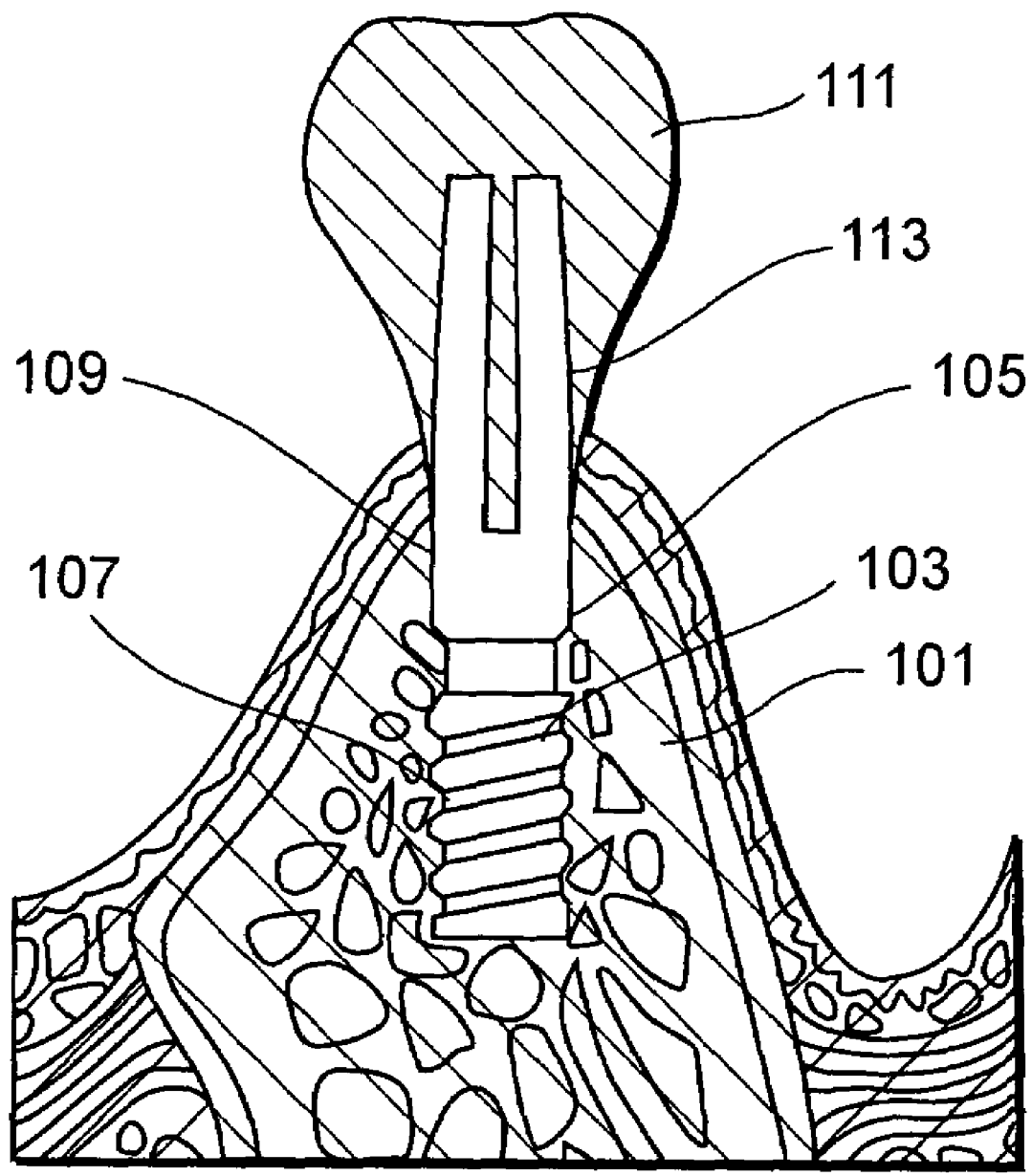
FIG. 6 is a view according to a prior art, showing a state of a tooth to which an implant therapy has been given.

A second embodiment of the present invention will now be described with reference to FIGS. 4 and 5. In the first embodiment, the second self tapping part 11 in a saw-blade shape is provided for all the crests of the male thread part 3. However, according to the second embodiment, the second self-tapping part 11 in a saw-blade shape is not provided, from the first crest to the halfway of the second crest, counted from the supporting stage 5. Thus, the first crest and the half of the second crest from the supporting stage, 5 are not in a saw-blade shape, but in an ordinary shape of screw thread. The number of crests not being in a saw-blade shape, is not limited to the present embodiment. The reason for providing the crest or crests not being in a saw-blade shape will be explained as below.

The upper end part of the artificial root of the tooth, that is the part near the supporting stage 5, is located relatively close to the oral cavity. There would be various bacteria or food waste particles remaining in the oral cavity, which would possibly go through the space between the artificial tooth and the gum-ridge, and eventually reach the upper end part of the artificial root of the tooth. In this case, if the screw thread is in a saw-blade shape, there might be a deposition of the bacteria or the food waste particles, which would result in the multiplication of bacteria. Thus, from the first crest to the halfway of the second crest near the supporting stage 5, the screw thread is in an ordinary shape, without having the second self tapping part 11 in a saw-blade shape, so that the uneven surface can be removed in order to prevent the deposition of bacteria and food waste particles.

The present invention is not limited to the first and second embodiments as described above.

For example, the first self tapping part 15 is not limited to the triple-blade structure. It is also possible to be provided with two blades, or with four or more blades.

In the first and the second embodiments, both the first self tapping part and the second self tapping part are provided. However, it is also possible to provide only one of these self tapping parts.

Further, the structures shown in the drawings are only examples of the invention, and the modification or alternation may be made as long as it is not departing from the spirit of the present invention.

What is claimed is:

1. An artificial root of a tooth, comprising:

an artificial root body of a tooth comprising a male thread part to be engaged with a jawbone, and a supporting stage on which an artificial tooth is mounted; and a self tapping part provided on said artificial root body of the tooth, wherein said self tapping part comprises a first self tapping part provided at a top of said artificial root body of the tooth, and a second self tapping part having a serrated shape provided on a screw thread of said male thread part, wherein said first self tapping part comprises a triple blade, wherein said second self tapping part has a serrated shape in a circumferential spiral-line direction of said screw thread in a spiral shape, and wherein said serrated shape is not provided at the first end or a first and a second crest counted from a base end of said screw thread.

2. The root of claim 1, wherein said circumferential saw-blade shape starts at least one thread away from said supporting stage to an end of said male thread opposing said supporting stage.

3. The root of claim 1, wherein said supporting stage is at a proximal end of said root, and said root further comprises another self tapping part at a distal end of said root.

4. The root of claim 3, wherein said another self tapping part comprises at least one blade.

5. The root of claim 4, wherein said another self tapping part comprises at least three blades.

6. The root of claim 1, further comprising an artificial tooth mounted on said supporting stage.

7. The root of claim 1, wherein said male thread part engages a jaw bone.

\* \* \* \* \*